United States Patent [19]
Mikami et al.

[11] Patent Number: 6,025,503
[45] Date of Patent: Feb. 15, 2000

[54] PROCESS FOR PRODUCING OPTICALLY ACTIVE TITANIUM ALKOXIDE COMPLEXES

[75] Inventors: Koichi Mikami; Satoru Matsukawa, both of Tokyo, Japan

[73] Assignee: Takasago International Corporation, Tokyo, Japan

[21] Appl. No.: 09/001,918

[22] Filed: Dec. 31, 1997

[30] Foreign Application Priority Data

Aug. 11, 1997 [JP] Japan .................................. 9-227014

[51] Int. Cl.$^7$ ...................................................... C07F 7/28
[52] U.S. Cl. ................................ 549/210; 556/54; 556/55
[58] Field of Search ............................... 549/210; 556/54, 556/55

[56] References Cited

U.S. PATENT DOCUMENTS 5,767,295 6/1998 Mitsuda et al. ......................... 549/425

OTHER PUBLICATIONS

Keck et al, Tet. Letters, vol. 34 (49), p.7827–7828, 1993.

*Primary Examiner*—Bernard Dentz
*Attorney, Agent, or Firm*—Sughrue, Mion, Zinn, Macpeak & Seas, PLLC

[57] ABSTRACT

Disclosed is a process for producing novel optically active titanium alkoxide complexes which are excellent in catalytic activity and enantio-selectivity in carbon-carbon bond forming reactions (for example, Ene reaction, hetero-Diels-Alder reaction, Aldol reaction) and have high stability. The present process comprises reacting (R),(S),(RS)-catalysts or mixtures thereof selected from among optically active or racemic titanium alkoxide complexes represented by the following general formula (1), etc.:

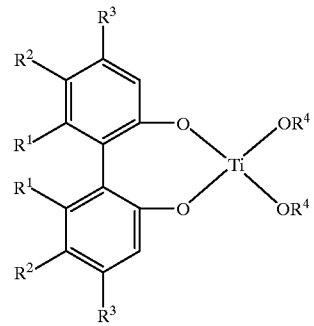

(1)

wherein $R^1$ represents a methyl, lower alkoxy or trihalogeno group; $R^2$ represents a hydrogen or halogen atom; $R^3$ represents a hydrogen atom or a methyl group; and $R^4$ represents a lower alkyl group, or $R^1$ and $R^2$ may form together a cyclo ring;
with chiral activators [(R),(S),(RS)-diols or mixtures thereof, but excluding reactions between a racemic modification and another racemic modification] to thereby activate exclusively one of the enantiomers.

7 Claims, No Drawings

PROCESS FOR PRODUCING OPTICALLY ACTIVE TITANIUM ALKOXIDE COMPLEXES

FIELD OF THE INVENTION

This invention relates to a process for producing complexes represented by the following general formulae (7), (8), (9), (10) and (11), in particular, optically active titanium complexes useful as catalysts in asymmetric reactions, which comprises reacting titanium alkoxide complexes represented by the following general formulae (1), (2) and (3) with chiral activators of optically active diols represented by the following general formulae (4), (5) and (6). The present invention further relates to processes for producing α-hydroxyesters, β-hydroxyesters and dihydropyrans by using these complexes.

BACKGROUND OF THE INVENTION

It has been known to use complexes composed of titanium atoms and organic ligands as catalysts in asymmetric reactions. It has been also known that optically active compounds, in particular, axially asymmetric compounds containing hydroxyl groups, are selected as the organic ligands therefor.

However, many of these axially asymmetric compounds containing hydroxyl groups are very expensive and, therefore, unsuitable for industrial uses. Accordingly, it is highly advantageous from the industrial viewpoint, if possible, to add a catalytic amount of an optically active axially asymmetric compound (i.e., a chiral activator) to a complex with the use of a ligand in racemic modification to thereby exclusively activate one of the enantiomers of the complex, thus achieving catalytic asymmetric synthesis with the use of the catalyst thus obtained.

There have been reported several cases of the asymmetric synthesis with the use of asymmetric ligands in racemic modification or metal complexes as precursors. For example, J. M. Brown et al. (*J. Chem. Soc., Chem. Commun.*, 1986 p. 1532) reported that CHIRAPHOS (2,3-bisdiphenylphosphinobutane) in racemic modification was treated with an optically pure (S)-iridium complex to thereby form its complex with (R)-CHIRAPHOS while the residual (S)-CHIRAPHOS was employed as a rhodium complex in the asymmetric hydrogenation of dehydroamino acids. According to H. Yamamoto et al. (*J. Am. Chem. Soc.*, 1989, vol. 111, p. 789), a chiral ketone was added to a racemic binaphthol/aluminum complex to thereby inactivate the (R)-binaphthol/aluminum complex via the formation of a complex, while the residual (S)-aluminum complex was employed in the asymmetric Diels-Alder reaction. Furthermore, J. W. Faller et al. (*J. Am. Chem. Soc.*, 1993, vol. 115, p. 804) reported that a phosphine ligand originating in methionine was added as an inactivating agent to a racemic rhodium complex to thereby inactivate one of the enantiomers, thus effecting the asymmetric hydrogenation of dehydroamino acids. However, it seems that the inactivated enantiomers are wasted in these three cases. In addition, these methods are not efficient, since any enantio-selectivity exceeding the level achieved by using optically pure catalysts cannot be established thereby.

SUMMARY OF THE INVENTION

Under these circumstances, an object of the present invention is to provide optically active compounds by using a titanium-containing complex having excellent asymmetric catalytic activity and high stability which is obtained by adding a racemic or optically active diol compound (chiral activator) to an optically active complex employed as a precursor, or adding an optically active diol compound (chiral activator) to a racemic complex employed as a precursor, to thereby selectively activate one of the enantiomers having the chiral activator coordinated therewith.

The present inventors have conducted extensive studies to solve the above-mentioned problems. As a result, they have found that optically active compounds having excellent catalytic activity and enantio-selectivity can be obtained by adding chiral activators such as racemic or optically active biphenol derivatives, binaphthol derivatives, octahydrobinaphthol derivatives or tartaric acid derivatives to racemic or optically active hydroxyl group-containing compound/titanium alkoxide complexes, but excluding reactions between a racemic modification with another racemic modification. After conducting the subsequent studies on the basis of this finding, they have successfully completed the present invention.

Accordingly, the gist of the present invention is as follows.

1) A process for producing optically active titanium alkoxide complexes represented by the following general formulae (7), (8), (9), (10) and (11):

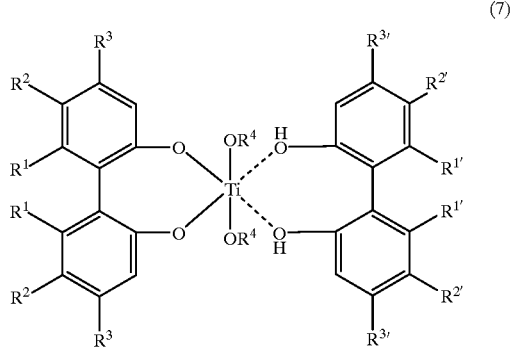

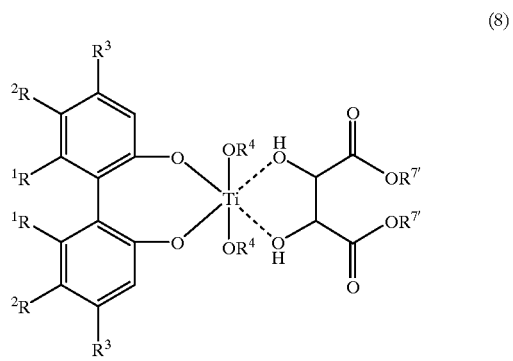

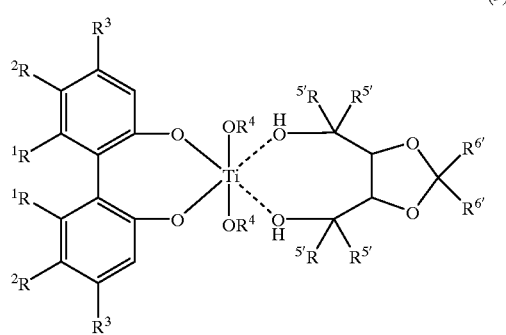

3
-continued (10)

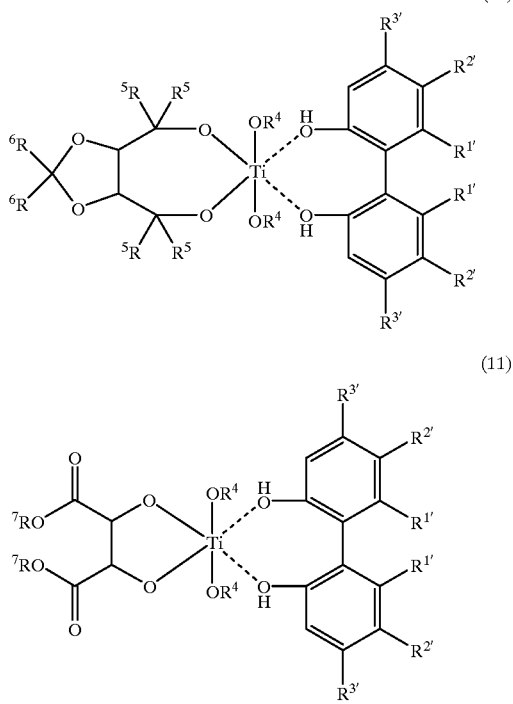

(11)

wherein R¹ represents a methyl, lower alkoxy or trihalogenomethyl group; R² represents a hydrogen or halogen atom, or R¹ and R² may together form a cyclo ring; R³ represents a hydrogen atom or a methyl group; R⁴ represents a lower alkyl group; R⁵ represents a phenyl, tolyl or naphthyl group; R⁶ represents a methyl or phenyl group; R⁷ represents a lower alkyl group; and $R^{1'}$, $R^{2'}$, $R^{3'}$, $R^{4'}$, $R^{5'}$, $R^{6'}$ and $R^{7'}$ have the same meanings respectively as those of $R^1$, $R^2$, $R^3$, $R^4$, $R^5$, $R^6$ and $R^7$ each as defined above;

which comprises reacting (R), (S), (RS)—catalysts or mixtures thereof selected from among optically active or racemic titanium alkoxide complexes selected from among those represented by the following general formulae (1), (2) and (3):

(1)

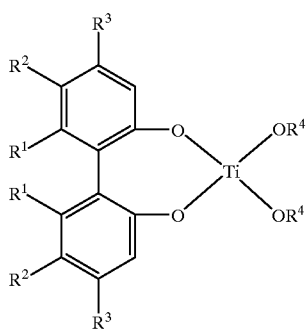

4
-continued (2)

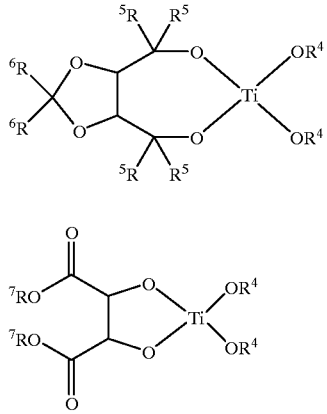

(3)

wherein $R^1$, $R^2$, $R^3$, $R^4$, $R^5$, $R^6$ and $R^7$ are each as defined above;

with chiral activators [(R),(S),(RS)-diols or mixtures thereof, but excluding reactions between a racemic modification and another racemic modification] represented by the following general formulae (4), (5) and (6):

(4)

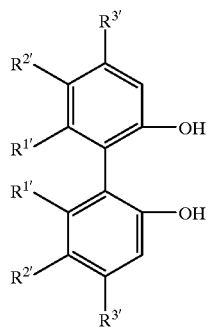

(5)

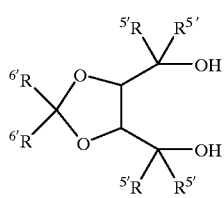

(6)

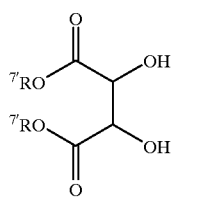

wherein $R^{1'}$, $R^{2'}$, $R^{3'}$, $R^{4'}$, $R^{5'}$, $R^{6'}$ and $R^{7'}$ are each as defined above;

to thereby activate exclusively one of the enantiomers.

(2) A process for producing β-hydroxyesters, which comprises employing the complexes as described in the above (1) as catalysts in the Aldol reaction between silylketene acetals and aldehydes as shown below:

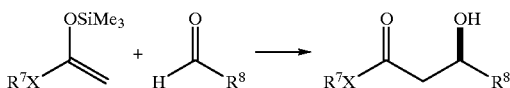

wherein $R^7$ represents a lower alkyl group; X represents an oxygen or sulfur atom; and $R^8$ represents an alkyl group having 1 to 10 carbon atoms.

(3) A process for producing α-hydroxyesters, which comprises employing the complexes as described in the above (1) as catalysts in the Ene reaction between α-alkylolefins and glyoxylates as shown below:

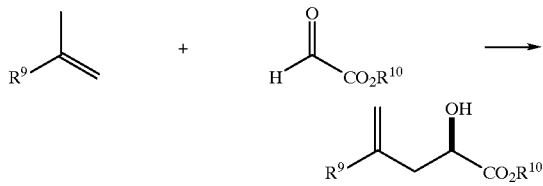

wherein $R^9$ represents a lower alkyl or phenyl group; and $R^{10}$ represents a lower alkyl group.

(4) A process for producing dihydropyrans, which comprises employing the complexes as described in the above (1) as catalysts in the hetero-Diels-Alder reaction between 1,3-butadienes and glyoxylates as shown below:

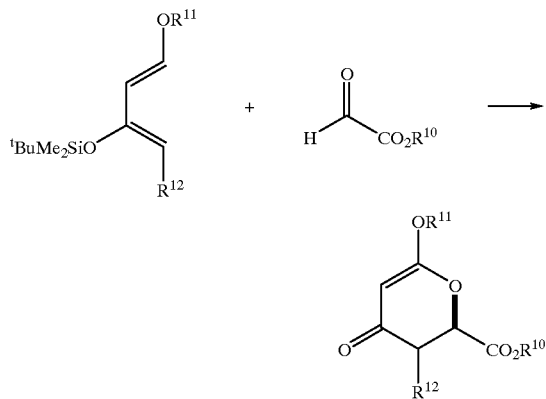

wherein $R^{10}$, $R^{11}$ and $R^{12}$ represents each a lower alkyl group.

DETAILED DESCRIPTION OF THE INVENTION

Now, the present invention will be described in greater detail.

In the general formula (1), $R^1$ is exemplified by methyl, methoxy, trichloromethyl, tribromomethyl and trifluoromethyl groups; $R^2$ is exemplified by hydrogen, chlorine, fluorine, bromine and iodine atoms; $R^3$ is exemplified by a hydrogen atom and a methyl group; and $R^4$ is exemplified by methyl, ethyl, propyl, isopropyl, butyl and tert-butyl groups; or $R^1$ and $R^2$ may form together a cyclo ring such as a phenyl or cyclohexyl ring. In the general formula (2), $R^5$ is exemplified by phenyl, tolyl and naphthyl groups; $R^6$ is exemplified by methyl and phenyl groups; and $R^4$ is as defined above. In the general formula (3), $R^7$ is exemplified by methyl, ethyl, n-propyl, i-propyl and n-butyl groups.

Now, the process for producing the optically active titanium alkoxide complexes of the present invention will be illustrated.

First, titanium alkoxide complexes represented by the general formulae (1), (2) and (3) are prepared. Next, these compounds are reacted with the compounds (chiral activators) represented by the general formulae (4), (5) and (6) to thereby give the titanium complexes (7), (8), (9), (10) and (11) of the present invention.

Although the compounds represented by the general formulae (1), (2) and (3) can be prepared by publicly known methods, it is preferable to prepare these compounds by mixing titanium tetraalkoxides with diols in organic solvents. More particularly speaking, the compounds of the general formulae (1), (2) and (3) can be synthesized in accordance with the method of T. Wang et al. (*Synthesis*, 1989, p. 291).

These compounds of the general formulae (1), (2) and (3) are then mixed with the axially dissymmetric diols (chiral activators) represented by the general formulae (4), (5) and (6). Thus the above-mentioned complexes can be obtained. When the compounds of the general formulae (1), (2) and (3) are optically active ones, then the compounds of the general formulae (4), (5) and (6) may be either racemic modifications or optically active ones. When the compounds of the general formulae (1), (2) and (3) are racemic modifications, the compounds of the general formulae (4), (5) and (6) should be optically active ones.

To prepare the complexes of the present invention, any organic solvent may be used without restriction, so long as it is almost inert to the titanium tetraalkoxides or the diols. It is preferable to use therefor aromatic hydrocarbons such as benzene, toluene and xylene; halogenated hydrocarbons such as methylene chloride, chloroform and carbon tetrachloride; or aprotic solvents such as tetrahydrofuran, diethyl ether and dimethoxyethane. The reaction temperature may be controlled in a range of from 0 to 30° C. The reaction time usually ranges from 10 to 180 minutes, preferably from 30 to 60 minutes, though it varies depending on the organic solvent, titanium tetraalkoxide, diol, etc. employed.

As the diol compounds employed as the chiral activators, it is preferable to use dimethyltartaric acid, diethyltartaric acid, dipropyltartaric acid, diisopropyltartaric acid, dibutyltartaric acid, di-tert-butyltartaric acid, 4,5-bisdiphenylhydroxymethyl-2,2-dimethyl-1,3-dioxolane, 4,5-bis(di-4-tolyl)hydroxymethyl-2,2-dimethyl-1,3-dioxolane, 4,5-bis(di-3,5-xylyl)hydroxymethyl-2,2-diethyl-1,3-dioxolane, 4,5-bisdiphenylhydroxymethyl-2-methyl-2-phenyl-1,3-dioxolane, 4,5-bisdiphenylhydroxymethyl-2,2-diphenyl-1,3-dioxolane, 1,1'-bi-2-naphthol, 6,6'-dicyano-1,1'-bi-2-naphthol, 6,6'-dibromo-1,1'-bi-2-naphthol, 5,5',6,6',7,7',8,8'-octahydro-2,2'-binaphthol, 4,4',6,6'-tetramethyl-5,5'-dichloro-2,2'-biphenol, 6,6'-dimethoxy-2,2'-biphenol, 4,4',5,5',6,6'-hexamethyl-2,2'-biphenol, 6,6'-dimethyl-2,2'-biphenol, 4,5-bis(dinaphthyl)hydroxymethyl-2,2-dimethyl-1,3-dioxolane, 6,6'-di(trifluoromethyl)-2,2'-biphenol, 4,4',6,6'-tetramethoxy-2,2'-biphenol, etc. The following tables (Tables 1 and 2) show the structural formulae of these compounds.

TABLE 1
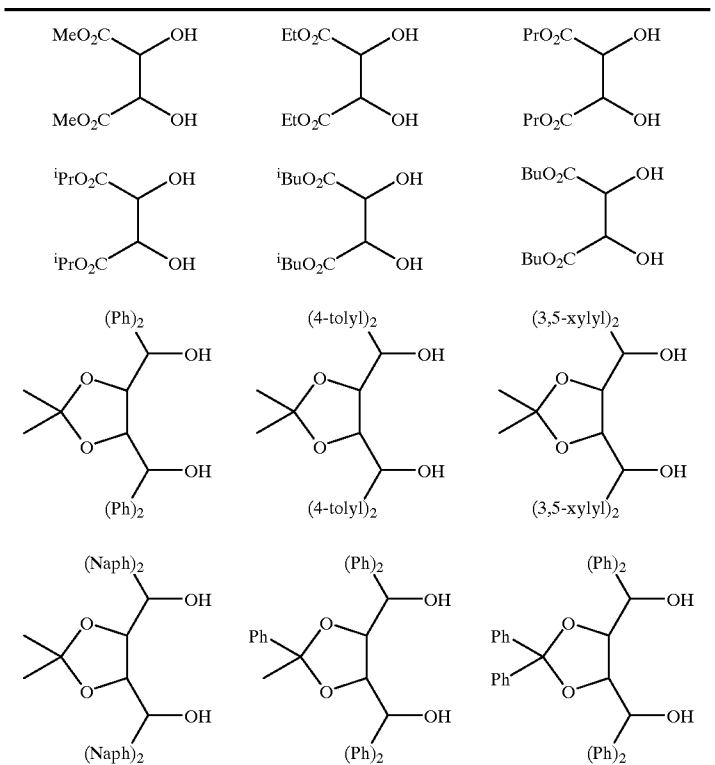
TABLE 2
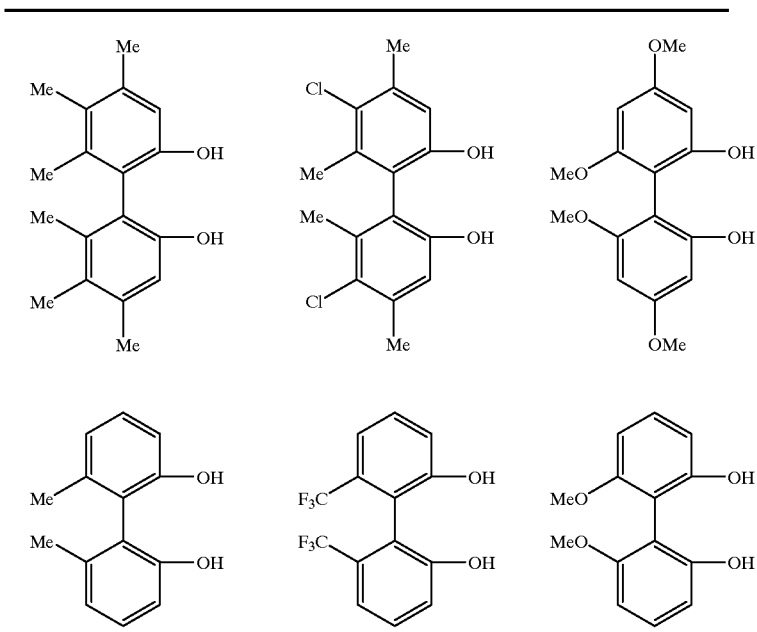

TABLE 2-continued

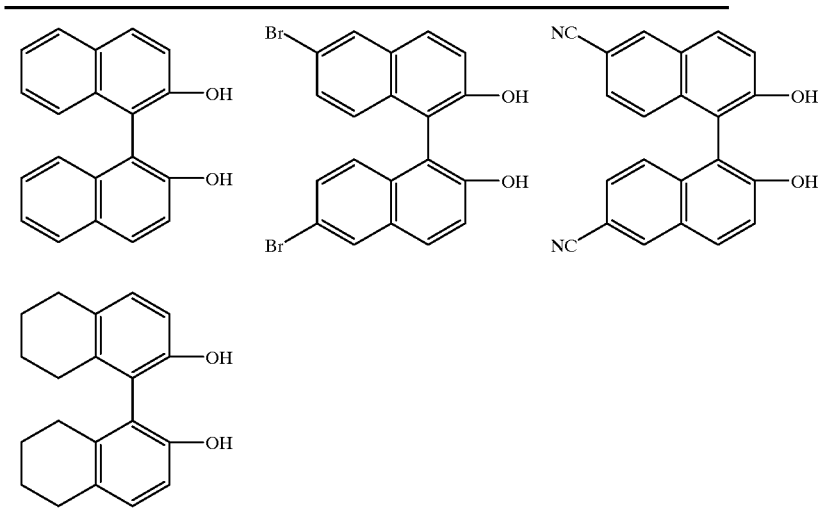

As the axially asymmetric diols employed as the chiral activators, it is preferable to use 1,1'-bi-2-naphthol, 6,6'-dibromo-1,1'-bi-2-naphthol, octahydro-1,1'-bi-2-naphthol, tetramethyl-5,5'-dichloro-2,2'-biphenol, 6,6'-dimethoxy-2,2'-biphenol, hexamethyl-2,2'-biphenol or 6,6'-dimethyl-2,2'-biphenol. Either (R)- or (S)-compounds may be selected for both of the diols and the axially asymmetric diols and, in its turn, (R)- or (S)-titanium complexes can be obtained respectively. It is preferable that both of these compounds have the same symbol. These compounds may be appropriately selected depending on the absolute configuration of the target product. The following tables (Tables 3 and 4) show the structural formulae of these compounds.

TABLE 3

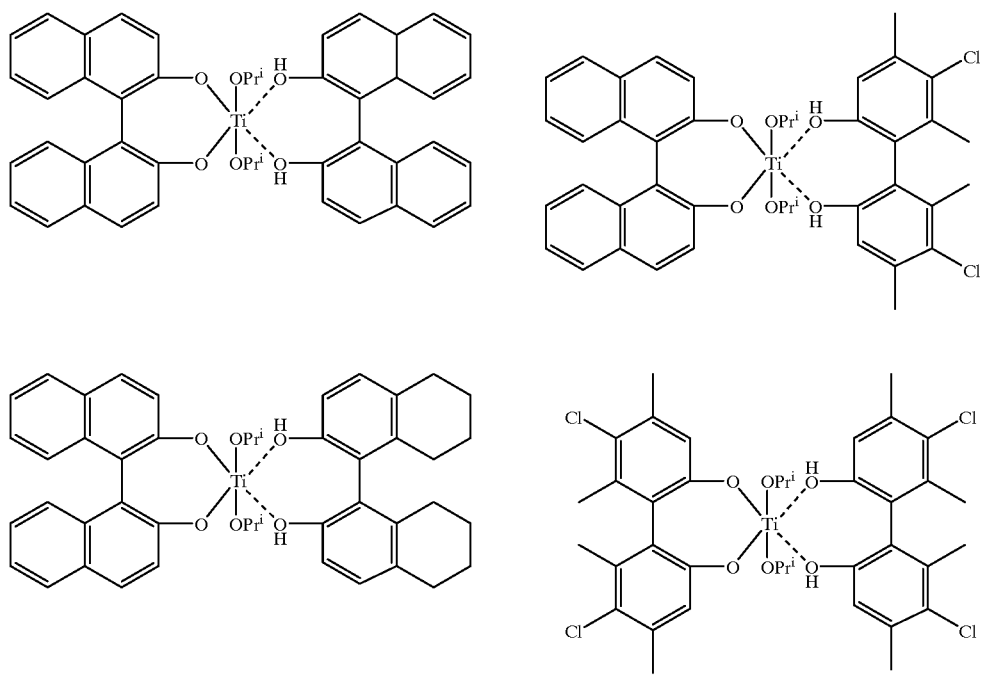

TABLE 3-continued

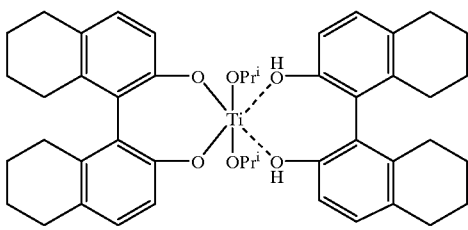
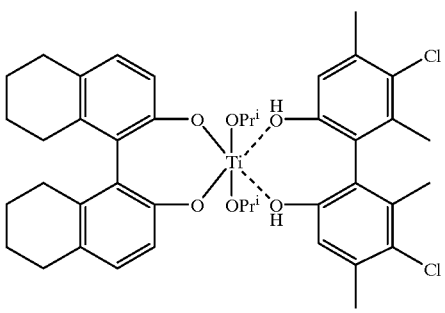

TABLE 4

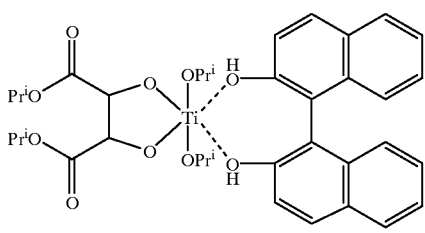
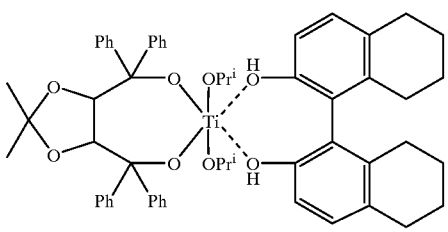

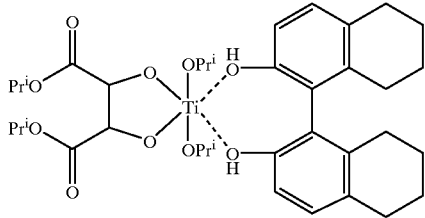
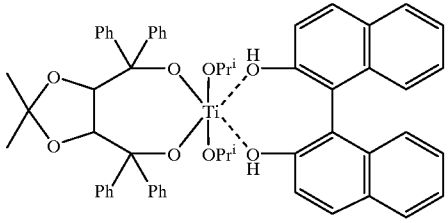

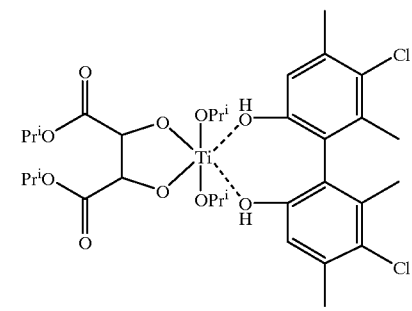
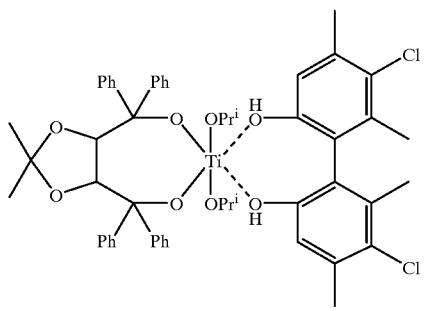

The coexistence of the thus produced titanium complexes of the present invention (7), (8), (9), (10) and (11) in reaction systems contributes to the advantageous progress of carbon-carbon bond forming reactions (for example, Ene reaction, hetero-Diels-Alder reaction, Aldol reaction). Among all, these complexes can be appropriately employed in the Aldol reaction between silylketene acetals and aldehydes, the Ene reaction between α-alkylolefins and glyoxylates and the hetero-Diels-Alder reaction between 1,3-butadienes and glyoxylates, as will be shown in (a) to (c) hereinbelow. More particularly speaking, the existence of the above-mentioned titanium complexes (7), (8), (9), (10) and (11) in the reaction systems allows the formation of carbon-carbon bonds and thus optically active compounds having the desired absolute configuration can be arbitrarily prepared.

(a) A process for producing β-hydroxyesters, wherein complexes as described in the above (1) are employed as catalysts in the Aldol reaction between silylketene acetals and aldehydes as shown below:

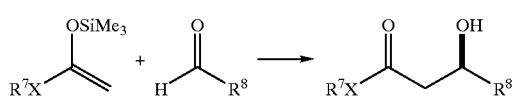

wherein $R^7$ represents a lower alkyl group; X represents an oxygen or sulfur atom; and $R^8$ represents an alkyl group having 1 to 10 carbon atoms.

(b) A process for producing α-hydroxyesters, wherein complexes as described in the above (1) are employed as catalysts in the Ene reaction between α-alkylolefins and glyoxylates as shown below:

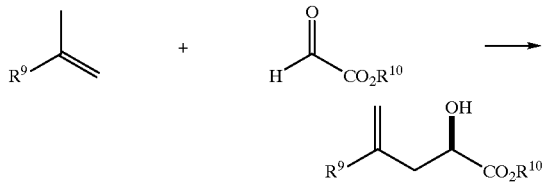

wherein $R^9$ represents a lower alkyl or phenyl group; and $R^{10}$ represents a lower alkyl group.

(c) A process for producing dihydropyrans, wherein complexes as described in the above (1) are employed as catalysts in the hetero-Diels-Alder reaction between 1,3-butadienes and glyoxylates as shown below:

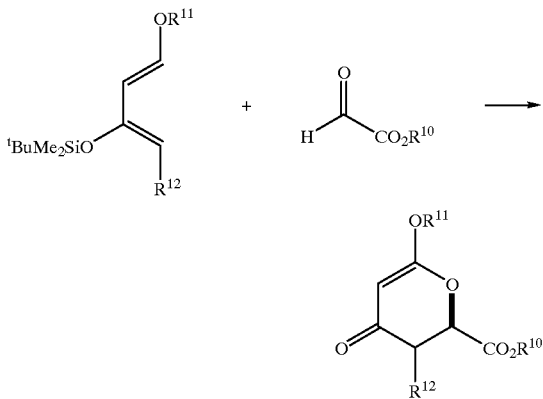

wherein $R^{10}$, $R^{11}$ and $R^{12}$ represents each a lower alkyl group.

The organic solvent to be used in these reactions are not particularly restricted, so long as they are almost inert to the titanium tetraalkoxides or the diols. It is preferable to use therefor aromatic hydrocarbons such as benzene, toluene and xylene; halogenated hydrocarbons such as methylene chloride, chloroform and carbon tetrachloride; or aprotic solvents such as tetrahydrofuran, diethyl ether and dimethoxyethane.

In these reactions, the titanium complexes (I) of the present invention may be used in an amount of from 20 to 0.1% by mol, preferably from 10 to 0.5% by mol, based on the above-mentioned substrates.

The reactions are carried out usually at −50 to 50° C., preferably at −10 to 20° C., and completed within 30 to 180 minutes, though the reaction conditions may be appropriately controlled depending on the amounts of the employed reactants, etc.

To further illustrate the present invention in greater detail, and not by way of limitation, the following Examples will be given.

Each product was analyzed by using the instruments as will be specified below.

$^1$H-Nuclear magnetic resonance spectrum (hereinafter referred to simply as $^1$H-NMR): Model GEMINI 300 (300 MHz) (manufactured by Varian).

$^{13}$C-Nuclear magnetic resonance spectrum (hereinafter referred to simply as $^{13}$C-NMR): Model GEMINI 300 (75 MHz) (manufactured by Varian).

Infrared absorption spectrum (hereinafter referred to simply as IR): FT/IR-5000 (manufactured by JASCO, Inc.).

Angle of rotation: Model DIP-370 (manufactured by JASCO, Inc.).

EXAMPLE 1

(1) Synthesis of (R)-1,1'-bi(2-naphtholate) (hereinafter referred to simply as BINOLate) titanium diisopropoxide complex 286 mg (1 mmol) of (R)-bi(2-naphthol), which had been dehydrated by boiling together with toluene, was dissolved in 20 ml of toluene and 284 mg (1 mmol) of titanium tetraisopropoxide was added thereto. After removing the isopropanol by boiling together, toluene was distilled off under reduced pressure. The residue was recrystallized from diethyl ether and pentane to thereby give 382 mg of a yellow solid (yield: 87%).

$^1$H-NMR ($C_7D_8$): δ1.12 (bs, 12H), 4.49 (br, 2H), 7.02 (m, 2H), 7.39 (d, J=8.7 Hz, 2H), 7.48 (d, J=8.7 Hz, 2H), 7.75 (d, J=8.4 Hz, 2H).

(2) Synthesis of (R)-bi(2-naphthol) (hereinafter referred to simply as BINOL)-coordinated BINOLate titanium diisopropoxide complex 225 mg (0.5 mmol) of the (R)-BINOLate titanium diisopropoxide complex and 143 mg (0.5 mmol) of (R)-binaphthol were stirred in heavy toluene.

$^1$H-NMR ($C_7D_8$) δ: 0.90 (br, 12H), 3.62 (br, 2H), 5.06 (br, 2H), 6.30–7.80 (m, 24H).

$^{13}$C-NMR ($C_7D_8$) δ: 25.7, 82.8, 112.6, 118.0, 118.6, 118.7, 119.5, 124.1, 125.1, 125.4, 127.6, 128.4, 128.7, 129.3, 130.6, 131.1, 131.3, 134.1, 134.7, 153.5, 162.6.

(3) Synthesis of (R)-5,5'-dichloro-4,4',6,6'-tetramethyl-2,2'-biphenol-coordinated BINOLate Titanium Diisopropoxide Complex 225 mg (0.5 mmol) of the (R)-BINOLate titanium isopropoxide complex and 156 mg (0.5 mmol) of (R)-5,5'-dichloro-4,4',6,6'-tetramethyl-2,2'-biphenol were stirred in toluene.

$^1$H-NMR ($C_7D_8$) δ: 0.93 (br, 12H), 2.04 (s, 6H), 2.22 (s, 6H), 3.72 (br, 2H), 5.05–5.60 (br, 2H), 6.61 (s, 2H), 6.80–7.30 (m, 8H), 7.61 (m, 4H).

$^{13}$C-NMR ($C_7D_8$) δ: 17.7, 21.2, 25.2, 81.6, 116.2, 118.3, 123.9, 126.1, 127–128, 131.2, 134.3, 138.1, 140.3, 152.9, 161.4.

EXAMPLE 2

(1) Synthesis of (S)-2,2-dimethyl-1,3-dioxolane-4,5-diylbis (diphenylmethylate) (hereinafter referred to simply as TADDOLate) titanium diisopropoxide complex 467 mg (1 mmol) of (S)-4,5-bis (diphenylhydroxymethyl)-2,2-dimethyl-1,3-dioxolane (TADDOL) and 284 mg (1 mmol) of titanium tetraisopropoxide were stirred in toluene.

$^1$H-NMR ($C_7D_8$) δ: 0.74 (s, 6H), 1.00 (bs, 12H), 3.84 (br, 2H), 5.42 (s, 2H), 7.07 (m, 12H), 7.55 (d, J=7.8 Hz, 2H), 7.74 (m, 6H).

$^{13}$C-NMR ($C_7D_8$) δ: 25.2, 27.2, 78.4, 81.3, 81.8, 109.5, 127.3, 129.1, 142.6, 145.8.

(2) Synthesis of (S)-binaphthol-coordinated (S)-TADDOLate titanium diisopropoxide complex 286 mg (1 mmol) of (S)-bi(2-naphthol) and 466 mg (1 mmol) of (S)-TADDOL were dissolved in 20 ml of toluene and 284 mg (1 mmol) of titanium tetraisopropoxide was added thereto. The obtained mixture was heated and isopropanol was removed by boiling together. Next, the solvent was distilled off under reduced pressure to thereby give 661 mg of the (S)-binaphthol-coordinated (S)-TADDOLate titanium diisopropoxide complex as a yellow solid (yield: 83%).

$^1$H-NMR ($C_7D_8$): δ0.67 (br, 6H), 5.20–5.60 (br, 2H), 6.30–7.80 (br, 32H).

$^{13}$C-NMR (C$_7$D$_8$): δ27.2, 78.4, 81.9, 109.7, 111.9, 118.5, 126.9, 127.0, 127.3, 127.5, 127.6, 127.9, 129.5, 131.1, 134.5, 137.3, 143.7, 147.1, 159.8.

EXAMPLE 3

Synthesis of (S)-tert-butyl-3-hydroxydodecanethioate 28.6 mg (0.1 mmol) of the racemic modification of binaphthol and 28.4 mg (0.1 mmol) of titanium tetraisopropoxide were stirred in 2 ml of toluene for 20 minutes. After adding 14.4 mg (0.05 mmol) of (R)-binaphthol, the mixture was stirred for 20 minutes to thereby give a solution of (R)-BINOL-coordinated BINOLate titanium diisopropoxide complex.

201 mg (1 mmol) of 1-tert-butylthio-1-trimethylsilyloxyethene and 142 mg (1 mmol) of nonylaldehyde were cooled to 0° C. Then the complex solution prepared above was added thereto and the resulting mixture was stirred for 2 hours. The reaction mixture was poured into a buffer solution (pH 7) at 0° C. The solution thus obtained was filtered through celite and the filtrate was extracted with ether thrice. The organic layer was washed with a saturated aqueous solution of sodium chloride and dried over anhydrous magnesium sulfate. After distilling off the solvent under reduced pressure, the residue was treated with 10% HCl—MeOH and purified by silica gel column chromatography (hexane/ethyl acetate=20/1). Thus 181 mg of (S)-tert-butyl-3-hydroxydodecanethioate was obtained (yield: 66%). When measured with CHIRALPAK OD column (manufactured by Daicel Chemical Industries) [hexane:i-PrOH=200:1, flow rate: 0.7 ml/min], the optical purity of this product was 97% e.e.

[α]$_D^{26}$: +15.0° (c 1.0, CHCl$_3$).

$^1$H-NMR (CDCl$_3$): δ0.87 (t, J=7.0 Hz, 3H), 1.26–1.45 (m, 14H), 1.47 (s, 9H), 2.54 (dd, J=8.4, 15.7 Hz, 1H), 2.63 (dd, J=3.3, 15.7 Hz, 1H), 2.78 (br, 1H), 3.99 (m, 1H).

$^{13}$C-NMR (CDCl$_3$): δ14.2, 22.8, 25.6, 29.4, 29.5, 29.7, 29.9, 32.6, 36.6, 48.6, 51.0, 68.9, 200.6.

IR (neat) 3470, 2930, 1670, 1450, 1370, 1270, 1160, 760 cm$^{-1}$.

Comparative Example 1

The procedure of Example 3 was repeated but preparing 45 mg (0.1 mmol) of (R)-BINOLate titanium diisopropoxide complex and using it as the complex. Thus, 145 mg of the aimed (S)-tert-butyl-3-hydroxydodecanethioate was obtained (53%, 91% e.e.).

EXAMPLE 4

Synthesis of n-butyl 2-hydroxy-4-phenyl-4-pentenoate

To 118 mg (1 mmol) of α-methylstyrene and 130 mg (1 mmol) of n-butylglyoxylate was added at 0° C. the solution of the complex in toluene obtained in Example 1 (2). After stirring for 1 hour, the reaction mixture was poured into a saturated aqueous solution of sodium bicarbonate and filtered through celite. Then the filtrate was extracted with ether thrice and dried over anhydrous magnesium sulfate. After distilling off the solvent under reduced pressure, the residue was purified by silica gel column chromatography (hexane/ethyl acetate=15/1). Thus 213 mg of n-butyl 2-hydroxy-4-phenyl-4-pentenoate was obtained (yield: 82%). When measured with CHIRALPAK AS column (manufactured by Daicel Chemical Industries) [hexane:i-PrOH=3:1, flow rate: 0.5 ml/min], the optical purity of this product was 97.5% e.e.

[α]$_D^{26}$: -21.2° (c 0.7, CHCl$_3$).

$^1$H-NMR (C$_7$D$_8$): δ0.93 (t, J=7.2 Hz, 3H), 1.34 (m, 2H), 1.56 (m, 2H), 2.72 (d, J=6.0 Hz, 1H), 2.83 (ddd, J=0.9, 7.5, 14.4 Hz, 1H), 3.06 (ddd, J=1.2, 4.5, 14.4 Hz, 1H), 4.03 (dddd, J=6.3, 6.6, 10.8, 13.2 Hz, 1H), 4.26 (ddd, J=4.5, 6.0, 7.5 Hz, 1H), 5.20 (d, J=1.2 Hz, 1H), 5.39 (d, J=1.2 Hz, 1H), 7.25–7.43 (m, 5H).

$^{13}$C-NMR (CDCl$_3$): δ13.6, 19.8, 30.4, 40.5, 65.4, 69.2, 116.5, 126.4, 127.6, 128.3, 140.3, 143.6, 174.5.

IR (neat): 3470, 2970, 1740, 1450, 1270, 1210, 1090, 780, 710 cm$^{-1}$.

Comparative Example 2

The procedure of Example 4 was repeated but preparing 45 mg (0.1 mmol) of (R)-BINOLate titanium diisopropoxide complex and using it as the complex. Thus, 52 mg of the aimed n-butyl 2-hydroxy-4-phenyl-4-pentenoate was obtained (20%, 94% e.e.).

EXAMPLE 5

To 258 mg (1.2 mmol) of (E)-1-methoxy-3-tert-butyldimethylsilyloxy-1,3-butadiene and 130 mg (1 mmol) of n-butylglyoxylate was added at 0° C. the solution of the complex in toluene obtained above. After stirring for 2 hours, 0.1 ml of trifluoroacetic acid was added thereto. Next, the reaction mixture was stirred for 5 minutes, then poured into a saturated aqueous solution of sodium bicarbonate and filtered through celite. Then the filtrate was extracted with ether thrice and dried over anhydrous magnesium sulfate. After distilling off the solvent under reduced pressure, the residue was purified by silica gel column chromatography (hexane/ethyl acetate=10/1). Thus 79 mg of n-butyl 3,4-dihydro-4-oxo-2H-pyran-2-carboxylate was obtained (yield: 40%). When measured with CHIRALPAK AD column (manufactured by Daicel Chemical Industries) [hexane:i-PrOH=10:1, flow rate: 1.0 ml/min], the optical purity of this product was 50% e.e.

[α]$_D^{26}$: -45.0° (c 1.0, CHCl$_3$).

$^1$H-NMR (CDCl$_3$): δ0.93 (t, J=7.3 Hz, 3H), 1.38 (m, 2H), 1.65 (m, 2H), 2.86 (d, J=7.8 Hz, 2H), 4.22 (t, J=6.7 Hz, 2H), 5.02 (t, J=7.8 Hz, 1H), 5.48 (d, J=6.1 Hz, 1H), 7.39 (d, J=6.1 Hz, 1H).

$^{13}$C-NMR (CDCl$_3$): δ13.7, 19.1, 30.5, 38.5, 66.2, 76.2, 108.1, 161.9, 168.1, 189.5.

IR (neat): 2970, 1760, 1680, 1400, 1280, 1210, 1040 cm$^{-1}$.

The present invention provides novel complexes containing titanium which are excellent in catalytic activity and enantio-selectivity in carbon-carbon bond forming reactions (for example, Ene reaction, hetero-Diels-Alder reaction, Aldol reaction) and have high stability.

What is claimed is:

1. A process for producing optically active titanium alkoxide complexes represented by the following general formulae (7), (8), (9), (10) and (11):

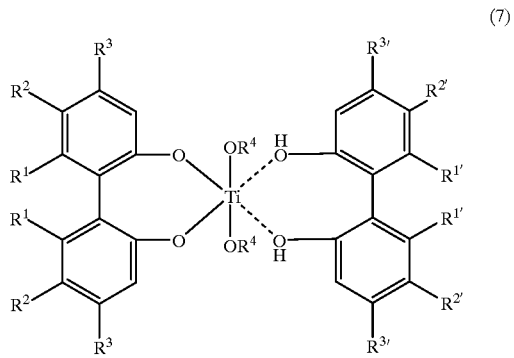

-continued (8)
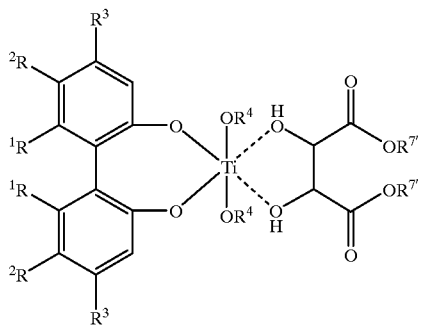

(9)
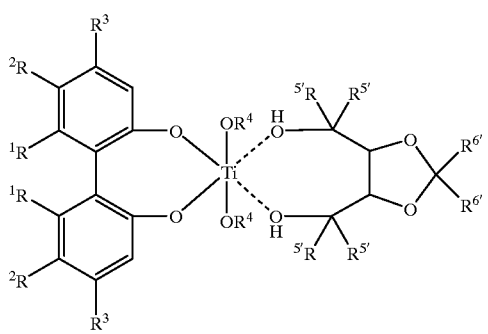

(10)
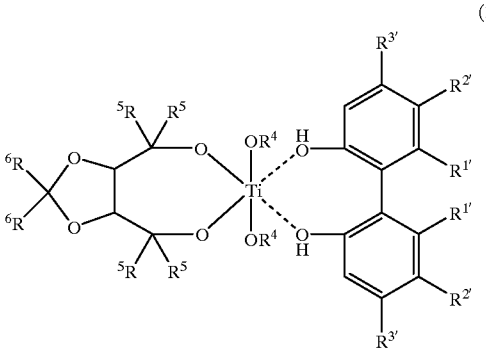

(11)
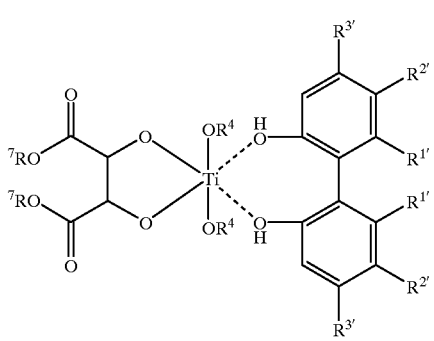

wherein $R^1$ represents a methyl, lower alkoxy or trihalogenomethyl group; $R^2$ represents a hydrogen or halogen atom, or $R^1$ and $R^2$ may together form a cyclo ring; $R^3$ represents a hydrogen atom or a methyl group; $R^4$ represents a lower alkyl group; $R^5$ represents a phenyl, tolyl or naphthyl group; $R^6$ represents a methyl or phenyl group; $R^7$ represents a lower alkyl group; and $R^{1'}$, $R^{2'}$, $R^{3'}$, $R^{4'}$, $R^{5'}$, $R^{6'}$ and $R^{7'}$ have the same meanings respectively as those of $R^1$, $R^2$, $R^3$, $R^4$, $R^5$, $R^6$ and $R^7$ each as defined above;

which comprises reacting (R),(S),(RS)-catalysts or mixtures thereof selected from among optically active or racemic titanium alkoxide complexes represented by the following general formulae (1), (2) and (3):

(1)
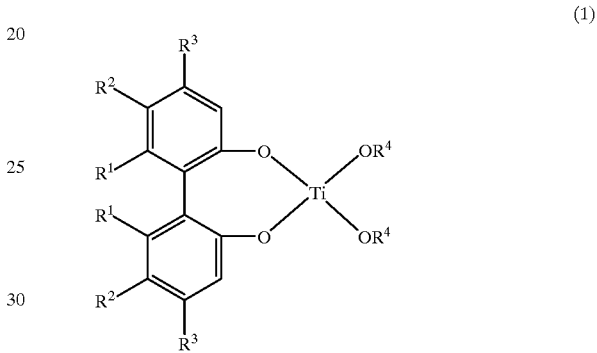

(2)
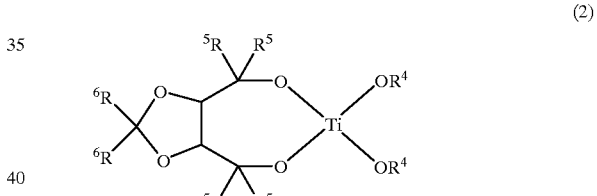

(3)
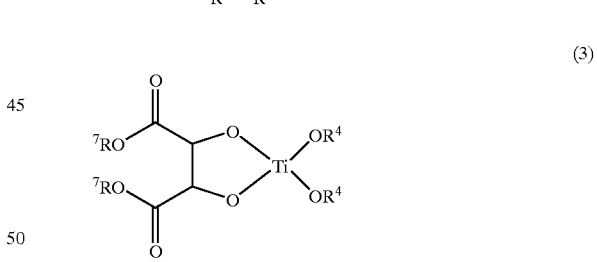

wherein $R^1$, $R^2$, $R^3$, $R^4$, $R^5$, $R^6$ and $R^7$ are each as defined above;

with chiral activators [(R),(S),(RS)-diols or mixtures thereof, excluding reactions between a racemic modification and another racemic modification] represented by the following general formulae (4), (5) and (6):

(4)

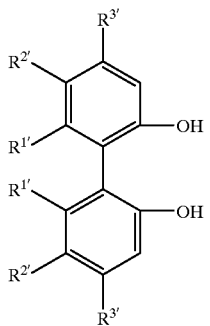

(5)

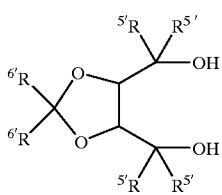

(6)

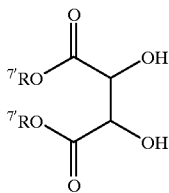

wherein $R^{1'}$, $R^{2'}$, $R^{3'}$, $R^{4'}$, $R^{5'}$, $R^{6'}$ and $R^{7'}$ are each as defined above;

to thereby activate exclusively one of the enantiomers.

2. The process according to claim 1, wherein said titanium alkoxide complex represented by the general formula (1), (2) or (3) is an optically active titanium alkoxide complex and said chiral activator represented by the general formula (4), (5) or (6) is a racemic chiral activator.

3. The process according to claim 1, wherein said titanium alkoxide complex represented by the general formula (1), (2) or (3) is a racemic optically active titanium alkoxide complex and said chiral activator represented by the general formula (4), (5) or (6) is an optically active chiral activator.

4. A process for producing optically active titanium alkoxide complexes represented by the general formulae (7), (8), (9), (10) and (11):

(7)

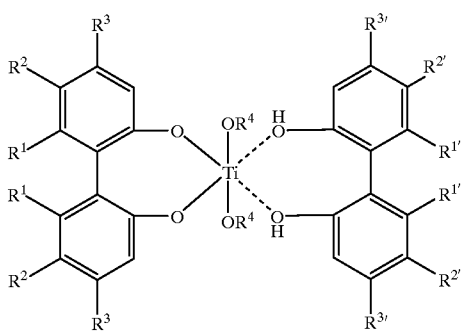

(8)

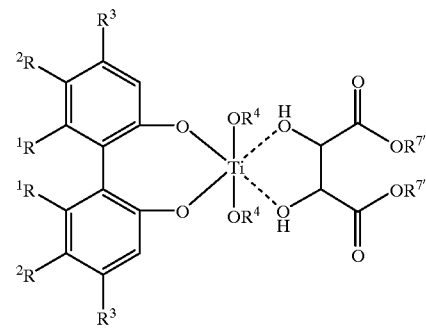

(9)

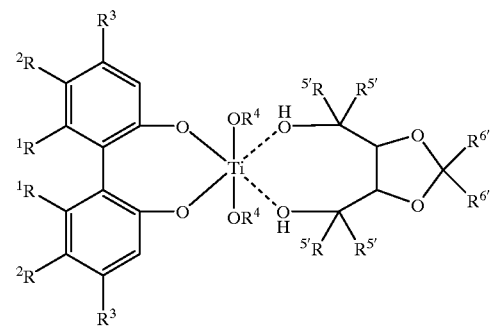

(10)

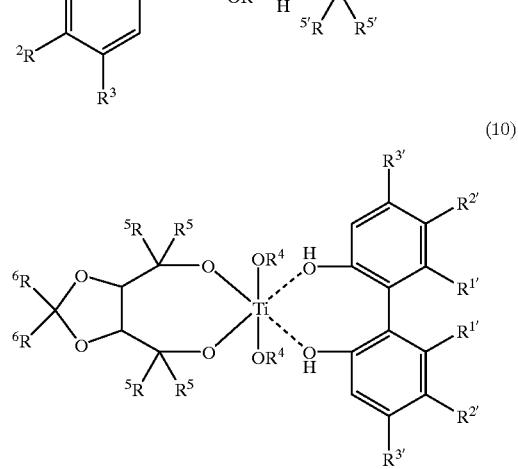

(11)

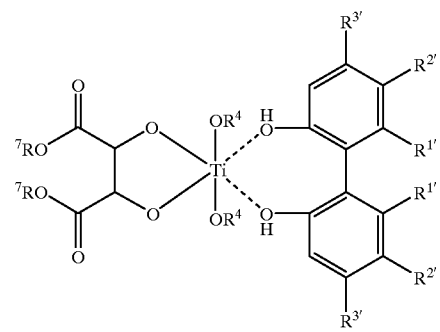

wherein $R^1$ represents a methyl, lower alkoxy or trihalogenomethyl group; $R^2$ represents a hydrogen or halogen atom, or $R^1$ and $R^2$ may together form a cyclo ring; $R^3$ represents a hydrogen atom or a methyl group; $R^4$ represents a lower alkyl group; $R^5$ represents a phenyl, tolyl or naphthyl group; $R^6$ represents a methyl or phenyl group; $R^7$ represents a lower alkyl group; and $R^{1'}$, $R^{2'}$, $R^{3'}$, $R^{4'}$, $R^{5'}$, $R^{6'}$ and $R^{7'}$ have the same meanings respectively as those of $R^1$, $R^2$, $R^3$, $R^4$, $R^5$, $R^6$ and $R^7$ each as defined above;

which comprises reacting an optically active titanium alkoxide complex represented by the following general formula (1), (2) or (3):

(1)
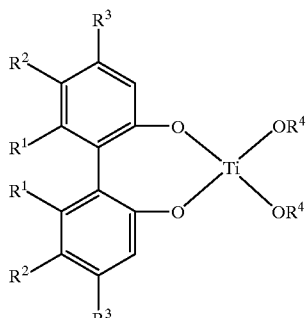

(2)
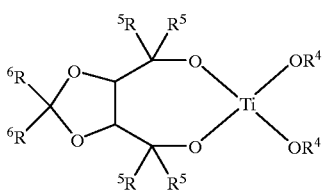

(3)
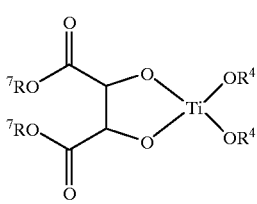

wherein $R^1$, $R^2$, $R^3$, $R^4$, $R^5$, $R^6$ and $R^7$ are each as defined above;

with an optically active chiral activator represented by the following general formulae (4), (5) or (6):

(4)
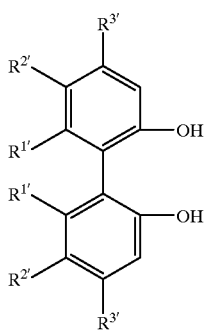

(5)
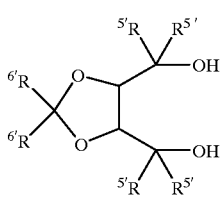

(6)
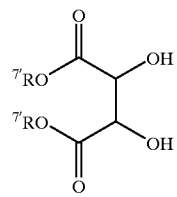

wherein $R^{1'}$, $R^{2'}$, $R^{3'}$, $R^{4'}$, $R^{5'}$, $R^{6'}$ and $R^{7'}$ are each as defined above.

5. A process for producing optically active titanium alkoxide complexes represented by the general formulae (7), (8), (9), (10) and (11):

(7)
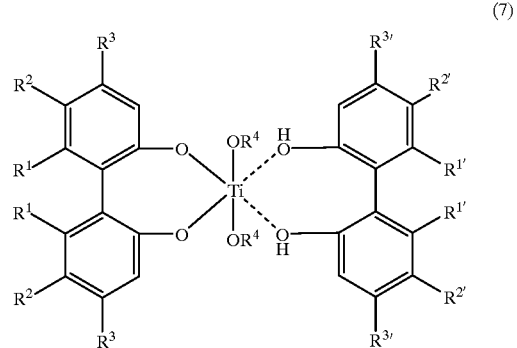

(8)
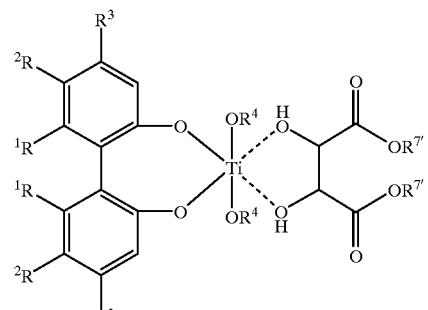

(9)
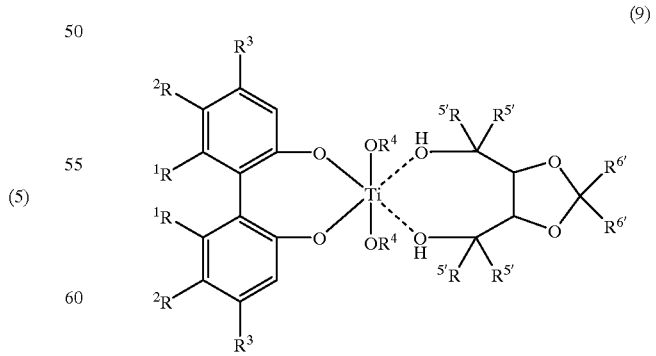

-continued

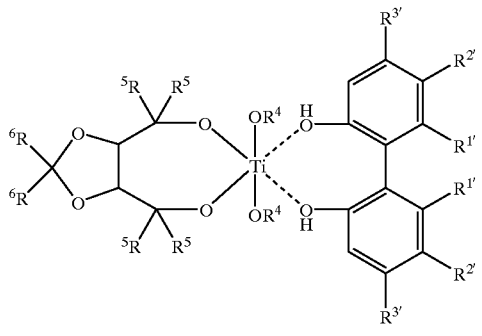
(10)

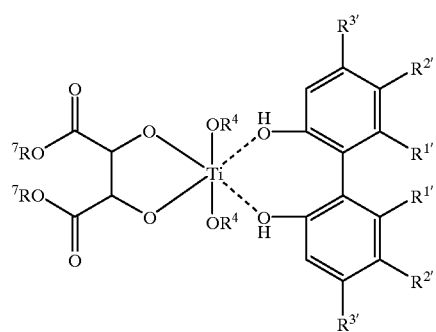
(11)

wherein R[1] represents a methyl, lower alkoxy or trihalogenomethyl group; R[2] represents a hydrogen or halogen atom, or R[1] and R[2] may together form a cyclo ring; R[3] represents a hydrogen atom or a methyl group; R[4] represents a lower alkyl group; R[5] represents a phenyl, tolyl or naphthyl group; R[6] represents a methyl or phenyl group; R[7] represents a lower alkyl group; and R[1'], R[2'], R[3'], R[4'], R[5'], R[6'] and R[7'] have the same meanings respectively as those of R[1], R[2], R[3], R[4], R[5], R[6] and R[7] each as defined above;

which comprises preparing a racemic or optically active complex represented by the general formula (1), (2) or (3):

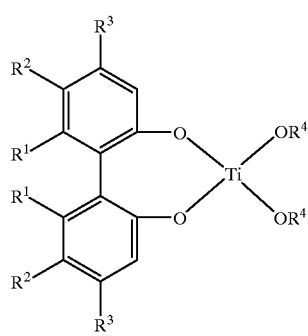
(1)

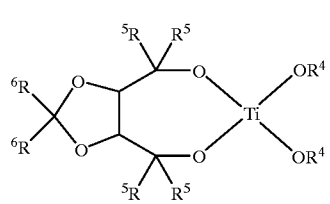
(2)

-continued

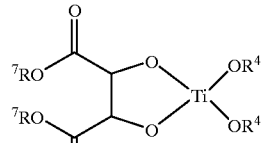
(3)

wherein R[1], R[2], R[3], R[4], R[5], R[6] and R[7] are each as defined above;

and adding to the resulting racemic or optically active complex an optically active diol in a half equivalent amount.

6. A process for producing optically active titanium alkoxide complexes represented by the general formulae (7), (8), (9), (10), and (11) in two steps:

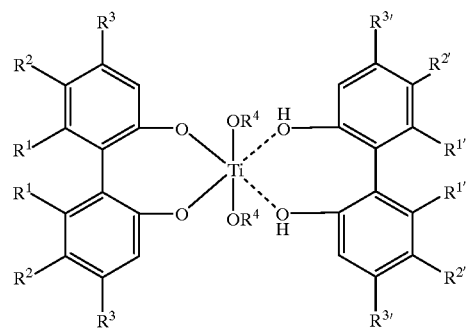
(7)

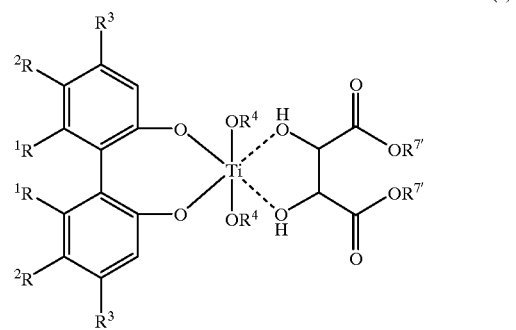
(8)

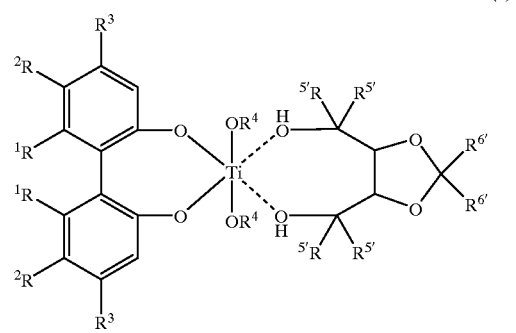
(9)

(10)

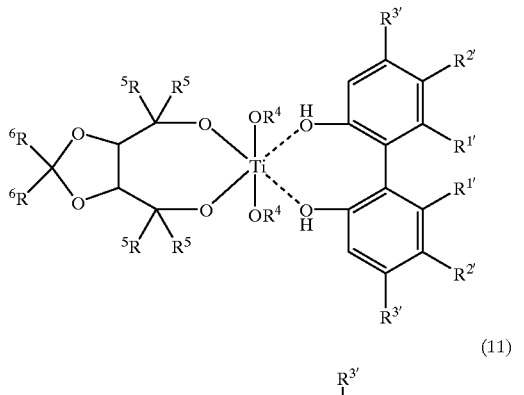

(11)

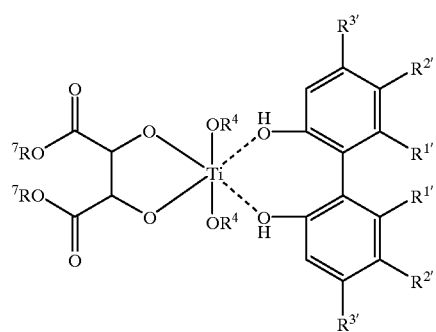

wherein $R^1$ represents a methyl, lower alkoxy or trihalogenomethyl group; $R^2$ represents a hydrogen or halogen atom, or $R^1$ and $R^2$ may together form a cyclo ring; $R^3$ represents a hydrogen atom or a methyl group; $R^4$ represents a lower alkyl group; $R^5$ represents a phenyl, tolyl or naphthyl group; $R^6$ represents a methyl or phenyl group; $R^7$ represents a lower alkyl group; and $R^{1'}$, $R^{2'}$, $R^{3'}$, $R^{4'}$, $R^{5'}$, $R^{6'}$ and $R^{7'}$ have the same meanings respectively as those of $R^1$, $R^2$, $R^3$, $R^4$, $R^5$, $R^6$ and $R^7$ each as defined above;

which comprises preparing a racemic or optically active complex represented by the general formula (1), (2) or (3):

(1)

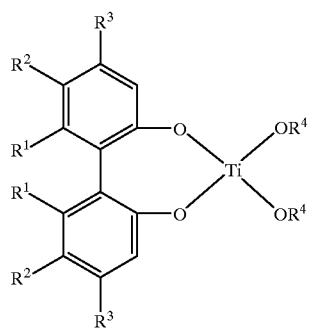

(2)

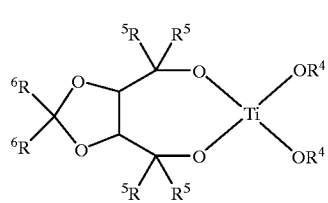

(3)

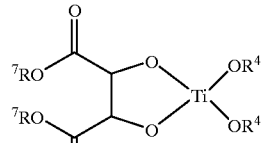

wherein $R^1$, $R^2$, $R^3$, $R^4$, $R^5$, $R^6$ and $R^7$ are each as defined above;

and adding to the resulting racemic or optically active complex an optically active diol.

7. A process for producing optically active titanium alkoxide complexes represented by the general formulae (7), (8), (9), (10) and (11) in two steps:

(7)

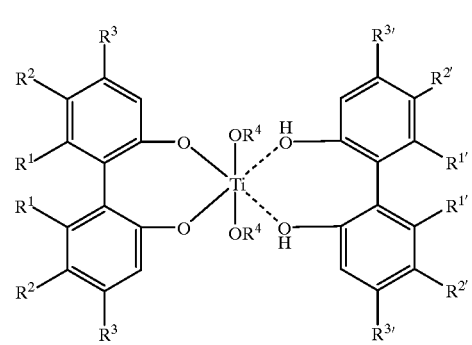

(8)

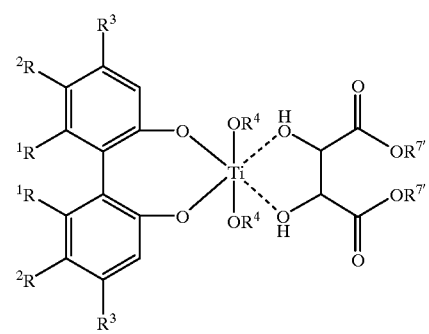

(9)

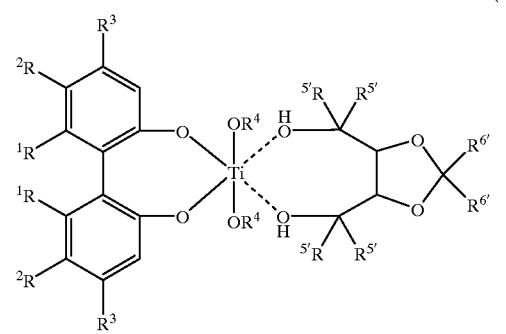

-continued

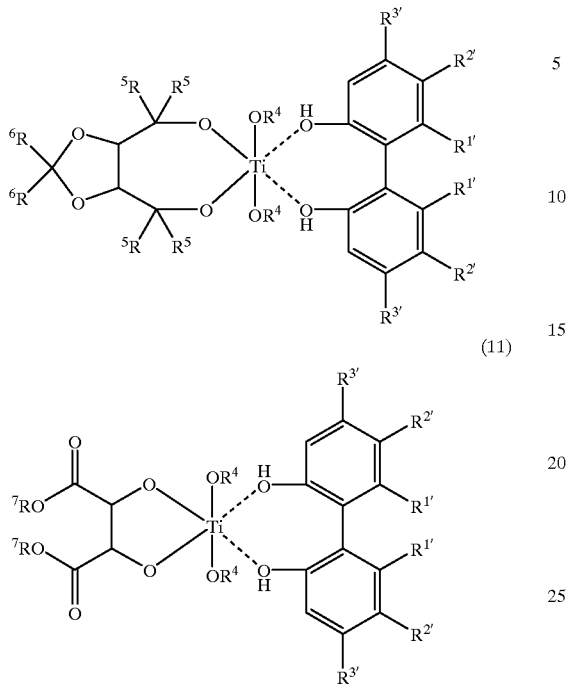

(10)

(11)

wherein $R^1$ represents a methyl, lower alkoxy or trihalogenomethyl group; $R^2$ represents a hydrogen or halogen atom, or $R^1$ and $R^2$ may together form a cyclo ring; $R^3$ represents a hydrogen atom or a methyl group; $R^4$ represents a lower alkyl group; $R^5$ represents a phenyl, tolyl or naphthyl group; $R^6$ represents a methyl or phenyl group; $R^7$ represents a lower alkyl group; and $R^{1'}$, $R^{2'}$, $R^{3'}$, $R^{4'}$, $R^{5'}$, $R^{6'}$ and $R^{7'}$ have the same meanings respectively as those of $R^1$, $R^2$, $R^3$, $R^4$, $R^5$, $R^6$ and $R^7$ each as defined above;

which comprises preparing a racemic or optically active complex represented by the general formula (1), (2) or (3):

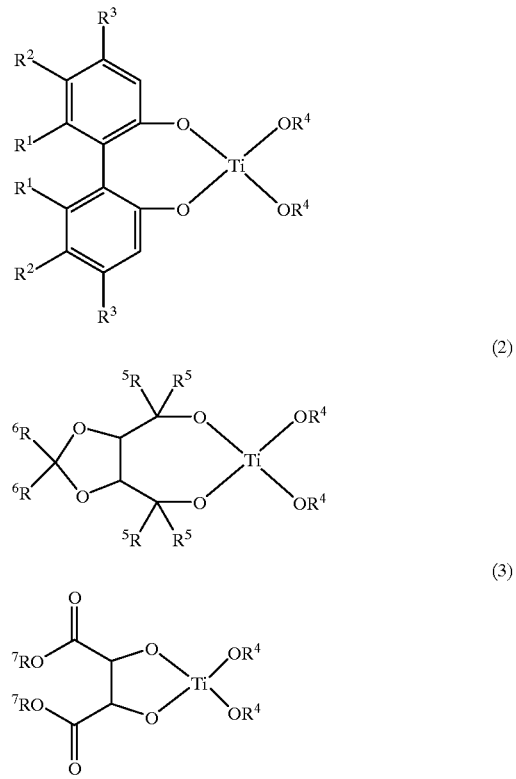

(1)

(2)

(3)

wherein $R^1$, $R^2$, $R^3$, $R^4$, $R^5$, $R^6$ and $R^7$ are each as defined above; and adding to the resulting racemic or optically active complex an optically active diol in a half equivalent amount.

* * * * *